United States Patent [19]

Braun

[11] Patent Number: 5,035,890

[45] Date of Patent: Jul. 30, 1991

[54] EMULSIFIER-FREE HAND AND BODY LOTION

[75] Inventor: Michael C. Braun, Port Jervis, N.Y.

[73] Assignee: Dow Corning Corporation, Midland, Mich.

[21] Appl. No.: 335,412

[22] Filed: Apr. 10, 1989

[51] Int. Cl.$^5$ .............................................. A61K 9/10
[52] U.S. Cl. ...................................... 424/401; 424/59; 424/60; 424/63; 424/81; 514/944
[58] Field of Search ............... 424/401, 63, 59, 60, 424/81; 514/944

[56] References Cited

U.S. PATENT DOCUMENTS

| | | | |
|---|---|---|---|
| Re. 27,026 | 1/1971 | Alfrey et al. | 260/2.5 |
| 2,809,943 | 10/1957 | Pye et al. | 260/2.1 |
| 3,175,898 | 3/1965 | Seymour et al. | 514/944 X |
| 3,418,262 | 12/1968 | Werotte et al. | 260/2.2 |
| 3,509,078 | 4/1970 | Roubinek et al. | 260/2.5 |
| 3,627,708 | 12/1971 | Morse et al. | 260/2.5 |
| 3,637,535 | 1/1972 | Corte et al. | 260/2.1 |
| 3,767,600 | 10/1973 | Albright | 260/2.2 |
| 3,989,649 | 11/1976 | Kailto et al. | 260/2.1 |
| 4,071,508 | 1/1978 | Steckler | 514/944 X |
| 4,208,309 | 6/1980 | Kraemer et al. | 260/8 |
| 4,224,415 | 9/1980 | Meitzner et al. | 521/38 |
| 4,554,156 | 11/1985 | Fischer et al. | 424/81 |
| 4,661,327 | 4/1987 | Horton | 423/7 |
| 4,690,818 | 9/1987 | Puchalski, Jr. et al. | 424/70 |
| 4,690,825 | 9/1987 | Won | 424/501 |
| 4,708,834 | 11/1987 | Cohen et al. | 514/944 X |
| 4,724,240 | 2/1988 | Abrutyn | 514/847 |
| 4,873,086 | 10/1989 | Good et al. | 514/944 X |

FOREIGN PATENT DOCUMENTS

| | | |
|---|---|---|
| 1168157 | 5/1984 | Canada . |
| 0252463 | 1/1988 | European Pat. Off. . |
| 2608533 | 9/1976 | Fed. Rep. of Germany . |
| 8801164 | 2/1988 | PCT Int'l Appl. . |

Primary Examiner—Thurman K. Page
Attorney, Agent, or Firm—Jim L. DeCesare

[57] ABSTRACT

An emulsifier-free hand and body lotion in the form of a clear gel dispersion. The dispersion includes a mixture of a gelled water system, a powdered carrier material of a cross-linked hydrophobic copolymer, and at least one active ingredient dispersed uniformly throughout and entrapped within said copolymer powder. The active ingredient can be one or more of a mixture of skin compatible oils, skin compatible humectants, emollients, moisturizing agents, and sunscreens.

7 Claims, No Drawings

EMULSIFIER-FREE HAND AND BODY LOTION

BACKGROUND OF THE INVENTION

This invention relates to a hand and body lotion in the form of a gelled dispersion, and while including a water phase and oily materials, is otherwise free of potentially skin irritating emulsifying agents normally present in lotion emulsions.

The concept of producing spheres or beads by means of suspension polymerization techniques is well known in the prior art. An exemplary one of such processes is disclosed in U.S. Pat. No. 2,809,943, issued Oct. 15, 1957. However, it was found that when a material was added which is a solvent for the monomers, but acts as a precipitant for the resulting polymer, a novel form of bead was provided containing a network of microscopic channels. This discovery is set forth in U.S. Pat. No. 4,224,415, filed July 18, 1958, and issuing some twenty-two years later on Sept. 23, 1980.

This technology was expanded and the precipitant was variously described in the patent literature as a diluent, porogen, solvent, functional material, and volatile agent. For example, in U.S. Pat. No. Re. 27,026, issued Jan. 12, 1971, porous beads of a diameter less than ten microns are disclosed. In U.S. Pat. No. 3,418,262, issued Dec. 24, 1968, there is described a rigid sponge structure and wherein the porogenic agent employed is an acid. Intermediates in bead form were produced in U.S. Pat. No. 3,509,078, issued Apr. 28, 1970, using polymeric materials as the precipitant material during the in situ suspension polymerization process. The macroporous character of such bead constructions is graphically portrayed in U.S. Pat. No. 3,627,708, issued Dec. 14, 1971. In U.S. Pat. No. 3,637,535, issued Jan. 25, 1972, beads with a sponge structure are said to be capable of being compressed to an imperceptible powder. A rigid porous bead of a trifunctional methacrylate is taught in U.S. Pat. No. 3,767,600, issued Oct. 23, 1973. Paraffin wax is used to form the microscopic network of channels in U.S. Pat. No. 3,989,649, issued Nov. 2, 1976.

While many of the foregoing U.S. patents relate to ion exchange technology, a bead similar to those previously described is employed as a carrier for enzymes in U.S. Pat. No. 4,208,309, issued June 17, 1980. U.S. Pat. No. 4,661,327, issued Apr. 28, 1987, describes a macroreticular bead containing a magnetic core. The use of hard crosslinked porous polymeric beads in cosmetics as carriers is taught in U.S. Pat. No. 4,724,240, issued Feb. 9, 1988, wherein various emollients and moisturizers are entrapped therein. Beads having a rigid sponge structure are also described in U.S. Pat. No. 4,690,825, issued Sept. 1, 1987, and wherein the beads function as a delivery vehicle for drugs, repellants, and sunscreens.

The foreign patent literature includes West German Offenlegungsschrift No. P 2608533.6, published Sept. 30, 1976, and wherein porous polymeric beads produced by suspension polymerization release perfumes. Canadian Patent No. 1,168,157, issued May 29, 1984, describes hard, discrete, free flowing, bead constructions in which the beads entrap a series of functional materials which can be incorporated into toilet soap, body powder, and antiperspirant sticks. The Canadian Patent, it is noted, is the equivalent of European Patent No. 61,701, issued on July 16, 1986. In European Patent Application Publication No. 0252463A2, published Jan. 13, 1988, there is disclosed a hydrophobic bead which entraps numerous non-cosmetic materials such as pesticides and pheromones. Steroids are entrapped, for example, in the porous beads of PCT International Publication No. WO 88/01164, published on Feb. 25, 1988. Thus, it should be apparent that what began as a simple ion exchange bead has rapidly grown into a technology of varied application.

In accordance with the present invention, however, hydrophobic polymer powders are used in a novel manner in order to constitute an interface between oil and water in a hand and body lotion. Oily materials are entrapped within the powder which is a combined system of particles which can be defined as a lattice, and when the particles are added to a lotion formulation, the need for potentially skin irritating emulsifying agents traditionally employed in emulsion systems is eliminated. As a result, there can be formed dispersions of the particles in a gelled water system, with the particles acting as carrier for the oily ingredients sought to be included as constituents in the lotion formulation.

SUMMARY OF THE INVENTION

This invention relates to a hand and body lotion in the form of a dispersion, which retains the function of an emulsion, but which does not contain the characteristic emulsifying agents of an emulsion, which are potentially irritating to the skin.

Thus, there is provided an emulsifier-free hand and body lotion in the form of a clear gel dispersion. The dispersion includes a mixture of a gelled water system, a particulate carrier material of a cross-linked hydrophobic polymer lattice, and at least one active ingredient being dispersed uniformly throughout and entrapped within said polymer lattice. The active ingredient can be one or more or a mixture of skin compatible oils, skin compatible humectants, emollients, moisturizing agents, and sunscreens.

The carrier material is the form of a powder, the powder being a combined system of particles. The system of powder particles forms a lattice which includes unit particles of less than about one micron in average diameter, agglomerates of fused unit particles of sizes in the range of about twenty to eighty microns in average diameter, and aggregates of clusters of fused agglomerates of sizes in the range of about two hundred to twelve hundred microns in average diameter. Preferably, there is provided a plurality of the active ingredients, each being dispersed uniformly throughout and entrapped within said polymer lattice.

The gelled water system includes water, a gel-forming agent, and a preservative. This system may also include a chelating agent for improving the clarity of the gel, and a neutralizing agent. There can be added to the gelled water system an opacifying agent in order to provide the clear gel dispersion with a creamy appearance.

It is therefore the object of the present invention to provide a novel type of hand and body lotion, which can be made to appear as a conventional creamy lotion emulsion, but which is actually an opacified clear gel dispersion, and which is free of potentially skin irritating emulsifying agents of conventional lotion emulsions.

These and other objects, features, and advantages, of the present invention will become apparent when considered in light of the following detailed description.

DETAILED DESCRIPTION OF THE INVENTION

The powder material of the present invention which is employed as the carrier for the active ingredient can be broadly described as a crosslinked "post adsorbed" hydrophobic polymer lattice. The powder has entrapped and dispersed therein, an active which may be in the form of a solid, liquid, or gas. The lattice is in particulate form and constitutes free flowing discrete solid particles when loaded with the active material. The lattice may contain a predetermined quantity of the active material. The polymer has the structural formula

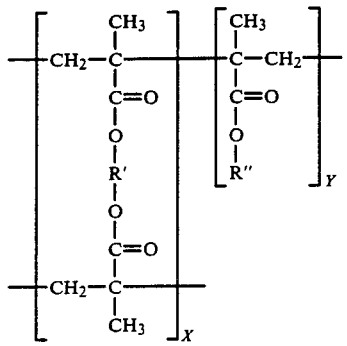

where the ratio of x to y is 80:20, R' is $-CH_2CH_2-$, and R'' is $-(CH_2)_{11}CH_3$.

The hydrophobic polymer is a highly crosslinked polymer, more particularly a highly crosslinked polymethacrylate copolymer. The material is manufactured by the Dow Corning Corporation, Midland, Mich., U.S.A., and sold under the trademark POLYTRAP ®. It is an ultralight free-flowing white powder, and the particles are capable of adsorbing high levels of lipophilic liquids and some hydrophilic liquids, while at the same time maintaining a free-flowing powder character. The powder structure consists of a lattice of unit particles less than one micron that are fused into agglomerates of twenty to eighty microns, and the agglomerates are loosely clustered into macro-particles or aggregates of about 200 to about 1200 micron size. The polymer powder is capable of containing as much as four times its weight of fluids, emulsions, dispersion, or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed.

EXAMPLE I

A hydrophobic crosslinked porous copolymer in powder form was produced by precipitation polymerization. According to this technique, 13.63 grams of ethylene glycol dimethacrylate, 4.37 grams of lauryl methacrylate, and 282 grams of isopropyl alcohol, were added to a reactor equipped with a paddle type stirrer. To the reactor was added 0.36 grams of benzoyl peroxide a catalytic initiator. The reactor was heated to 80° C. for six hours. The monomers were soluble in the isopropyl alcohol solvent but not the precipitated copolymer. The polymerization produced unit particles of a diameter less than one micron. Some unit particles adhered together to form agglomerates of 20-80 microns in diameter, and some agglomerates adhered and further fused and welded together into aggregates of loosely held assemblies of agglomerates. The aggregates were 200-800 microns in average diameter. The mixture was filtered to remove excess solvent. The wet powder cake was dried in a vacuum oven isolating a dry powder. Mineral oil was post adsorbed onto the dry powder and the post adsorbed powder was used in Example II. Other solvents such as toluene, cyclohexane, and heptane, can also be used. U.S. Pat. No. 4,724,240, lists other types of monomers which may be copolymerized.

Some unique features of the powder of Example I is its ability to adsorb from sixty to eighty percent of a liquid and yet remain free flowing. The material provides a regulated release of volatile ingredients entrapped therein and has the capability of functioning as a carrier for non-volatile oils. Loaded powders disappear when rubbed upon a surface. This phenomenon is believed to be due to the fact that large aggregates of the material scatter light rendering the appearance of a white powder, however, upon rubbing, these large aggregates decrease in size approaching the range of visible light and hence seem to disappear. The powder materials find applications in such diverse areas as cosmetics and toiletries, household and industrial products, pesticides, pheromones, and pharmaceuticals. The powder materials do not swell in common solvents and are capable of physically adsorbing active ingredients by the filling of interstitial voids therein by virtue of capillary action. The active ingredients are subsequently released therefrom by capillary action or wicking from the voids within the powder.

A cosmetic is defined as any substance, preparation, or treatment, intended to be applied to a person in order to cleanse, beautify, alter the appearance of, or promote the attractiveness of the person. Cosmetics include creams, powders, pastes, lotions, and coloring agents, which are intended to be applied to the body, specifically the face, scalp, hair, nails, or hands, and also encompasses deodorants, depilatories, and suntanning preparations. They may be rubbed, poured, sprinkled, or sprayed, into or on the human body.

A lotion is an aqueous or alcoholic-aqueous solution of substances intended to have some special effect upon the skin. Lotions consist of emulsified lotions, nonemulsified lotions, nonalcoholic, mildly alcoholic, and strongly alcoholic lotions. Typical of emulsified lotions are hand and face lotions, hair dressings, tonics, rinses, foot lotions, medicated lotions, baby lotions, suntan lotions, insect repellents, and liquid cream sachets. Cosmetic emulsified lotions are generally milky or creamy in appearance, and are formed of a stable mixture of two or more normally immiscible liquids held in suspension by small amounts of an emulsifying agent. The emulsions include a continuous phase and a disperse phase, and in an oil in water emulsion, the continuous phase is water whereas the disperse phase is the oil. In a water in oil emulsion, water is dispersed as fine globules in oil which is the continuous phase. The emulsion remains stable as long as the particles do not coalesce, which is the function of the emulsifying agent. Typical oil in water emulsifying agents are polyethylene glycol distearate, sorbitan monolaurate, and triethanolamine stearate. Water in oil emulsifying agents may consist of lanolin alcohols, ethylene glycol monostearate, sorbitan monooleate, and polyethylene glycol dilaurate. However, such conventional emulsifying agents have been found to be potentially irritating to the skin and therefore undesirable.

The hand and body lotion of the present invention includes all of the benefits of conventional lotion emulsions such as being beneficial for the skin, having a smooth and silky feel, being non-greasy, and possessing moisturization qualities, while at the same time eliminating the disadvantages of prior art lotion emulsions by the omission of the potentially skin irritating emulsifying agents. This is accomplished by providing a simple mixture of a gelled water system which constitutes the water phase, with an oil phase in the form of oily materials entrapped within a polymeric powder carrier. Since the oily materials are entrapped within the powder carrier, they are not in admixture directly with the water phase, and hence there is no need for an emulsifying agent for the oil-water system. The powder carrier material itself constitutes the interface between the water and oil phases, and the oil phase is not released from the powder until the lotion is applied and rubbed into the skin. The system has the appearance of a clear gel but with the addition of an opacifying agent, the clear gel can be masked and made to take on the appearance of a milky or creamy lotion emulsion, if desired. Such systems may be prepared and are set forth by way of the following example illustrating preparation of a hand and body lotion in accordance with the present invention.

EXAMPLE II

Into a container there was added a quantity of demineralized water. To the demineralized water there was added a chelating agent of disodium ethylenediamine tetra-acetic acid. The chelating agent is a product of Ciba-Geigy, Greensboro, N.C., and sold under the trademark SEQUESTRENE ®. The function of the chelating agent is to improve the clarity of the resulting gel. A preservative was added to the mixture of demineralized water and chelating agent. Preservatives which may be employed are alkyl esters of para-hydroxybenzoic acid, hydantoin derivatives, propionate salts, or quaternary ammonium compounds. Preferred preservatives are methyl and propyl para-hydroxybenzoate, imidazolidinyl urea, or quaternium 15. The demineralized water, the chelating agent, and a preservative, were present in the container in the following percentages by weight, respectively, 88.8%; 0.1%; and 0.1%. Into this mixture in the container was sprinkled 0.5 weight percent of a gel forming agent. The gel forming agent was a water soluble vinyl polymer manufactured by B. F. Goodrich Chemical Group, Cleveland, Ohio, and sold under the trademark CARBOPOL ® 940. Mechanical agitation was applied and the system was allowed to fully hydrate. Upon completion of hydration, there was slowly added to the hydrated system, 7.5 weight percent of the polymer powder of Example I containing mineral oil. The mineral oil-carrier powder were in the ratio of 3:1. The powder was mixed in the container with the other ingredients until the powder was uniformly dispersed. The resulting product was clear, with the particles of the mineral oil-loaded powder carrier, dispersed throughout the gel. A neutralizing agent of 1.0 weight percent of triethanolamine sold by Eastman Kodak Company, Rochester, N.Y., was added to the gelled dispersion, which thickened requiring increased agitation. The thickened gel-like dispersion was found to be suitable as a hand and body lotion. In order, to provide the gel-like dispersion with the appearance of a lotion, there was added to the gelled system 2.0 weight percent of opacifying agent. After thoroughly mixing the opacifying agent, the product had the creamy milky appearance of a lotion emulsion. The opacifying agent was a product manufactured and sold by the Morton Chemical Company, Chicago, Ill., and known as E-300 Opacifier. The opacifier is a sodium styrene-acrylate polyethylene glycol dimaleate copolymer including ammonium nonoxynol sulfate. The addition of the opacifier is optional depending upon aesthetic requirements.

While specific weight percentages are set forth for each ingredient in Example II, such ranges are exemplary only. For example, the gelling agent may constitute from about 0.1 to 0.5 weight percent. Triethanolamine may be present in weight percentages of from 0.2 to 1.0%. The opacifier may constitute from 0.5 to 2.0 weight percent; and from 0.1 to about 7.5 weight percent of the loaded acrylate copolymer carrier may be employed. The pH of the clear gel system is 5.5 to about 7.5; and the viscosity is from 5,000 to 50,000 centipoise measured at twenty-five degrees Centigrade. The content of water can be from eighty weight percent to ninety-five percent.

In Example II, the polymeric carrier powder was post adsorbed with a quantity of mineral oil. Mineral oil is one of numerous skin beneficial ingredients which may be post adsorbed and added to the system. Following are alternative combinations A–G of post adsorbed powder systems each containing one or more materials beneficial to the skin, and which may be substituted for the mineral oil loaded powder of the Example II. Weight percentages for each ingredient and the carrier powder are set forth. It should be noted that the ingredients are of the categories of skin compatible oils, skin compatible humectants, emollients, moisturizing agents, and sunscreens.

| COMPONENTS | WEIGHT PERCENT % |
|---|---|
| A. Glycerine | 66.7 |
| Acrylate Powder | 33.3 |
| B. Octyl Hydroxystearate | 75.0 |
| Acrylate Powder | 25.0 |
| C. Octyl Dimethyl Para-amino Benzoic Acid | 75.0 |
| Acrylate Powder | 25.0 |
| D. Vitamin E Acetate | 65.0 |
| Acrylate Powder | 35.0 |
| E. Arachidyl Propionate | 75.0 |
| Acrylate Powder | 25.0 |
| F. Octyl Hydroxystearate | 65.0 |
| Wheat Germ Glyceride | 5.0 |
| Acrylate Powder | 30.0 |
| G. Eucalyptus Oil | 35.0 |
| Menthol | 30.0 |
| Octyl Hydroxystearate | 10.0 |
| Acrylate Powder | 25.0 |

In some other alternative combinations H–V of powder loaded systems, at least one ingredient can be a silicone material. The term silicone denotes a polymer of the formula

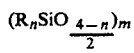

wherein n is an integer between zero and three, and m is two or more. The simplest silicone materials are the polydimethylsiloxanes. Polydimethylsiloxanes have the structure

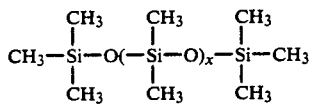

where x is an integer of from one to about one hundred thousand. The repeating unit of the polymer

```
Me
SiO
Me
``` is the dimethylsiloxane unit. The terminal unit (Me3SiO) is the trimethylsiloxy group. At low molecular weights, silicones are fluids, and at high molecular weights, they are gums which may be cross-linked to form elastomeric products. The methyl group in a silicone may be substituted by a variety of other substituents including for example, phenyl, vinyl, and hydrogen. Conventional silicones are the trimethylsiloxy terminated polydimethylsiloxanes. Such materials are available in viscosities ranging from 0.65 to 2,500,000 centistokes. Substituents on the silicon consist of methyl groups or oxygen. Termination of the polymer chain prevents viscosity change and other alterations of the physical properties of the silicone polymeric materials. The polydimethylsiloxanes exhibit characteristic properties of low viscosity change with temperature; thermal stability; oxidative stability; chemical inertness; non-flammability; low surface tension; high compressibility; shear stability; and dielectric stability. In resin forming polysiloxanes, some of the methyl groups are hydrolyzable and permit the formation of Si—O—Si cross-links upon heating in the presence of a catalyst, but in the organosilicon fluids and oils, substantially all of the methyl groups are non-hydrolyzable and the fluid is heat stable. In accordance with the present invention, the silicone based fluid preferred for use herein is a polydimethylsiloxane polymer having a molecular weight in the range of about 200 to about 200,000, and having a nominal viscosity in the range of from about 20 to 2,000,000 centistokes, preferably from about 500 to 50,000 centistokes, more preferably from about 3,000 to about 30,000 centistokes measured at twenty-five degrees centigrade. The siloxane polymer is generally end-blocked either with trimethylsilyl or hydroxyl groups but other end-blocking groups are also suitable. The polymer can be prepared by various techniques such as the hydrolysis of dimethyldihalosilanes and subsequent condensation of the resulting hydrolysis product, or by the cracking and subsequent polymerization of dimethylcyclosiloxanes. For the purposes of the present invention, the nominal viscosity of the polymer ranges from about two hundred to about fifteen hundred centistokes measured at twenty-five degrees centigrade, with viscosities of from about 350 to about 1,000 being most preferred.

Alternative combinations H–V of post adsorbed powder systems each containing one or more materials beneficial to the skin, including a silicone material, and which may be substituted for the mineral oil loaded powder of Example II are shown below. Weight percentages for each ingredient and the carrier powder are set forth. The ingredients are skin compatible oils, skin compatible humectants, emollients, moisturizing agents, and sunscreens.

| COMPONENTS | WEIGHT PERCENT % |
|---|---|
| H. Polydimethylsiloxane Fluid, viscosity 350 centistokes | 70.0 |
| Acrylate Powder | 30.0 |
| I. Polydimethylsiloxane Fluid, viscosity 350 centistokes | 15.0 |
| Glycerine | 15.0 |
| Fragrance | 5.0 |
| Acrylate Powder | 25.0 |
| Polydimethylcyclosiloxane, which is Cyclomethicone of the formula $(CH_3)_2SiO_x$ where x is five, and viscosity 6.0 centistokes | 40.0 |
| J. Acrylate Powder | 20.0 |
| Polydimethylcyclosiloxane, which is Cyclomethicone of the formula $(CH_3)_2SiO_x$ where x is five, and viscosity 6.0 centistokes | 80.0 |
| K. Acrylate Powder | 30.0 |
| Polydimethylcyclosiloxane, which is Cyclomethicone of the formula $(CH_3)_2SiO_x$ where x is five, and viscosity 6.0 centistokes | 20.0 |
| Glycerine | 10.0 |
| Octyl Hydroxystearate | 40.0 |
| L. Acrylate Powder | 35.0 |
| Polydimethylcyclosiloxane, which is Cyclomethicone of the formula $(CH_3)_2SiO_x$ where x is five, and viscosity 6.0 centistokes | 14.0 |
| Glycerine | 5.0 |
| Octyl Hydroxystearate | 9.0 |
| Mineral Oil | 37.0 |
| M. Acrylate Powder | 35.0 |
| Polydimethylcyclosiloxane, which is Cyclomethicone of the formula $(CH_3)_2SiO_x$ where x is five, and viscosity 6.0 centistokes | 20.0 |
| Glycerine | 5.0 |
| Mineral Oil | 40.0 |
| N. Acrylate Powder | 35.0 |
| Polydimethylcyclosiloxane, which is Cyclomethicone of the formula $(CH_3)_2SiO_x$ where x is five, and viscosity 6.0 centistokes | 25.0 |
| Mineral Oil | 40.0 |
| O. Mineral Oil | 30.0 |
| Glycerine | 5.0 |
| Fragrance | 5.0 |
| Acrylate Powder | 35.0 |
| Polydimethylcyclosiloxane, which is Cyclomethicone of the formula $(CH_3)_2SiO_x$ where x is five, and viscosity 6.0 centistokes | 25.0 |
| P. Mineral Oil | 25.0 |
| Glycerine | 5.0 |
| Acrylate Powder | 35.0 |
| Polydimethylcyclosiloxane, which is Cyclomethicone of the formula $(CH_3)_2SiO_x$ where x is five, and viscosity 6.0 centistokes | 20.0 |
| Polyphenylmethylsiloxane copolymer fluid which is Phenyltrimethicone, and viscosity 22.5 centistokes | 15.0 |

-continued

| COMPONENTS | WEIGHT PERCENT % |
| --- | --- |
| Q. Mineral Oil | 30.0 |
| Fragrance | 5.0 |
| Acrylate Powder | 35.0 |
| Polydimethylcyclosiloxane, which is Cyclomethicone of the formula $(CH_3)_2SiO_x$ where x is five, and viscosity 6.0 centistokes | 20.0 |
| Polyphenylmethylsiloxane copolymer fluid which is Phenyltrimethicone, and viscosity 22.5 centistokes | 10.0 |
| R. Octyl Adipate | 35.0 |
| Acrylate Powder | 35.0 |
| Polydimethylcyclosiloxane, which is Cyclomethicone of the formula $(CH_3)_2SiO_x$ where x is five, and viscosity 6.0 centistokes | 20.0 |
| Polyphenylmethylsiloxane copolymer fluid which is Phenyltrimethicone, and viscosity 22.5 centistokes | 10.0 |
| S. Oleyl Alcohol | 7.5 |
| Mineral Oil | 40.0 |
| Acrylate Powder | 30.0 |
| Polydimethylcyclosiloxane, which is Cyclomethicone of the formula $(CH_3)_2SiO_x$ where x is five, and viscosity 6.0 centistokes | 12.5 |
| A mixture of Polydimethylcyclosiloxane, which is Cyclomethicone of the formula $(CH_3)_2SiO_x$ where x is five, and viscosity 6.0 centistokes; and Dimethicone which is $CH_3[Si(CH_3)_2O]Si(CH_3)_3$ and viscosity 1800 cst | 10.0 |
| T. Mineral Oil | 45.5 |
| Acrylate Powder | 30.0 |
| Polydimethylcyclosiloxane, which is Cyclomethicone of the formula $(CH_3)_2SiO_x$ where x is five, and viscosity 6.0 centistokes | 19.0 |
| A mixture of Polydimethylcyclosiloxane, which is Cyclomethicone of the formula $(CH_3)_2SiO_x$ where x is five, and viscosity 6.0 centistokes; and Dimethicone which is $CH_3[Si(CH_3)_2O]Si(CH_3)_3$ and viscosity 1800 cst | 5.5 |
| U. Acrylate Powder | 33.0 |
| A mixture of Polydimethylcyclosiloxane, which is Cyclomethicone of the formula $(CH_3)_2SiO_x$ where x is five, and viscosity 6.0 centistokes; and Dimethicone which is $CH_3[Si(CH_3)_2O]Si(CH_3)_3$ and viscosity 1800 cst | 67.0 |
| V. Mineral Oil | 52.0 |
| Acrylate Powder | 35.0 |
| A mixture of Polydimethylcyclosiloxane, | 13.0 |

-continued

| COMPONENTS | WEIGHT PERCENT % |
| --- | --- |
| which is Cyclomethicone of the formula $(CH_3)_2SiO_x$ where x is five, and viscosity 6.0 centistokes; and Dimethicone which is $CH_3[Si(CH_3)_2O]Si(CH_3)_3$ and viscosity 1800 cst | |

It will be apparent from the foregoing that many other variations and modifications may be made in the structures, compounds, compositions, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. An emulsifier-free hand and body lotion in the form of a clear gel dispersion comprising a gelled water system, the gelled water system including water, and a gel-forming agent, a particulate carrier material of a highly cross-linked hydrophobic polymer powder, and at least one active ingredient being dispersed uniformly throughout and entrapped within said powder carrier, the active ingredient being selected from the group consisting of skin compatible oils, skin compatible humectants, emollients, moisturizing agents, and sunscreens.

2. The lotion of claim 1 wherein the carrier material is a combined system of particles, the system of powder particles including unit particles of less than about one micron in average diameter, agglomerates of fused unit particles of sizes in the range of about twenty to eighty microns in average diameter, and aggregates of clusters of fused agglomerates of sizes in the range of about two hundred to twelve hundred microns in average diameter.

3. The lotion of claim 2 wherein the gelled water system includes disodium ethylenediamine tetraacetic acid as a chelating agent for improving the clarity of the gel.

4. The lotion of claim 3 wherein the gelled water system includes triethanolamine as a neutralizing agent.

5. The lotion of claim 4 wherein there is added to the gelled water system sodium styreneacrylate polyethylene glycol dimaleate copolymer which includes ammonium nonoxynol sulfate as an opacifying agent in order to provide the clear gel dispersion with a creamy appearance.

6. The lotion of claim 5 wherein there is provided a plurality of said active ingredients each being dispersed uniformly throughout and entrapped within said powder carriers.

7. The lotion of claim 6 wherein the powder carrier is a polymethacrylate polymer, and the gelled water system includes a preservative selected from the group consisting of alkyl esters of parahydroxybenzoic acid, hydantoin derivatives, propionate salts, and quaternary ammonium compounds.

* * * * *